United States Patent [19]
Ramadoss et al.

[11] Patent Number: 6,124,482
[45] Date of Patent: *Sep. 26, 2000

[54] PROCESS FOR ISOLATION OF 10-DEACETYL BACCATIN-III

[75] Inventors: Sunder Ramadoss, New Delhi; Anand Vardhan, Delhi, both of India

[73] Assignee: Dabur Research Foundation, Ghaziabad, India

[*] Notice: This patent is subject to a terminal disclaimer.

[21] Appl. No.: 09/392,763

[22] Filed: Sep. 7, 1999

Related U.S. Application Data

[63] Continuation-in-part of application No. 09/212,321, Dec. 15, 1998, Pat. No. 6,002,024.

[30] Foreign Application Priority Data

Jul. 27, 1998 [IN] India .......................... IP-2194/DEL/98

[51] Int. Cl.⁷ .................................................. C07D 305/14
[52] U.S. Cl. .............................................................. 549/510
[58] Field of Search .............................................. 549/510

[56] References Cited

U.S. PATENT DOCUMENTS

| | | | |
|---|---|---|---|
| 5,453,520 | 9/1995 | Bombardelli et al. | 549/510 |
| 6,002,024 | 12/1999 | Ramadoss et al. | 549/510 |

OTHER PUBLICATIONS

*applicants U.S. application No. 9/212321.

*Primary Examiner*—Amelia Owens
*Attorney, Agent, or Firm*—Ladas & Parry

[57] ABSTRACT

A novel process for isolation of 10-deacetyl baccatin-III (10-DAB) and also complete separation of paclitaxel present in the primary extract, on a commercial scale from plant extract of Taxus species by solvent crystallization without employing chromatographic separation.

11 Claims, No Drawings

PROCESS FOR ISOLATION OF 10-DEACETYL BACCATIN-III

The present application is a continuation-in-part of the earlier U.S. patent application No. 09/212,321 filed on Dec. 15, 1998, now U.S. Pat. No. 6,002,024 in which process for the isolation of 14β-hydroxy 10-deacetyl baccatin-III has been described.

FIELD OF THE INVENTION

The present invention relates to the field of phytochemistry. More specifically, the invention provides a simple and cost-effective method for the isolation of the compound 10-deacetyl baccatin-III (10-DAB) from the leaves of *Taxus baccata*. 10-DAB is a backbone intermediate compound useful in the preparation of paclitaxel and docetaxel and their analogues.

BACKGROUND OF THE INVENTION 10-deacetyl baccatin-III(10-DAB) is a very important precursor for the synthesis of paclitaxel and docetaxel analogues, which show excellent cytotoxicity against human ovaries, lungs, colon and breast cancer cell lines [ref. J. Med. chem. 1977, 40, 267–278].

10-deacetyl baccatin-III is represented by the following structural formula:

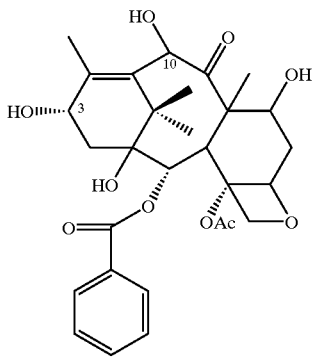

The compound 10-deacetyl baccatin-III is primarily found in the trunk and leaves of the plants of Taxus sp. in highest concentration. While the other parts of the plants also contain this compound, however, the concentration is less.

Most common methods of isolation of 10-DAB involves the extraction of biomass with alcohol or any protic solvent to yield an extract which is semipurified by solvent partition/maceration and finally selective crystallization or chromatography to yield 10-DAB. Some of the common methods employed in the art for extraction of 10-DAB are given herein below:

U.S. Pat. No. 5,393,895 relates to extracting the biomass with aliphatic alcohol followed by dilution with water and separating the insolubles. Thereafter, removing the total alcohol to yield an aqueous solution which is subjected to partition with organic solvents and selective crystallization to yield 10-DAB.

U.S. Pat. No. 5,736,366 relates to a process for obtaining 10-deacetyl baccatin-III. This process relates to extracting the biomass with water followed by adsorption on an appropriate substrate and desorbing using an organic solvent and finally deploying selective crystallization.

U.S. Pat. No. 5,453,521 relates to treating the biomass with aliphatic alcoholic and diluting with water, separating the insolubles from the hydroalcoholic solution and thereafter, removing the alcohol completely and extracting the aqueous solution with organic solvent followed by selective crystallization to obtain 10-DAB.

U.S. Pat. No. 5,393,896 relates to treating the biomass with water followed by treatment with organic solvent of the aqueous extract, the organic phase is further subjected to selective crystallization to yield 10-DAB.

WO 94/07881 relates to extraction of the biomass with water and thereafter adsorbing on a suitable substrate or without absorbing, and then treating with organic solvent, followed by selective crystallization to obtain 10-DAB.

WO 94/07882 relates to extraction of the biomass with methanol and followed by dilution with water, removing insolubles. The soluble portion is subjected to remove of alcohol totally to yield an aqueous solution which is subjected to partition with suitable organic solvent followed by selective crystallization to yield 10-DAB.

None of the above prior arts teach the isolation of paclitaxel present in the biomass, which is an important drug for the treatment of overian and breast cancer. In addition, the above processes do not lead to the complete separation of paclitaxel from 10-DAB, which is present in the primary extract. Further, the present invention provides a most economically and eco-frienly process to isolate 10-DAB from Taxus species.

OBJECTS OF THE PRESENT INVENTION

Accordingly, one objective of the present invention is to provide a simple and cost-effective process for the isolation of 10-DAB (10-deacetylbaccatin-III) for use as an intermediate in the synthesis of paclitaxel and docetaxel analogues.

Another objective of the present invention is to provide a process which does not involve tedious step of isolation by chromatographic technique at any stage for isolation 10-DAB.

Yet another objective of the present invention is to provide a process wherein the solvent used in various steps can be recycled.

It is also an objective of the present invention to provide a novel process which can be used for extraction of 10-DAB from any part of the plant of Taxus species.

Still another objective of the invention relates to a process which provides complete separation of paclitaxel from 10-DAB present in the primary extract so that both can be obtained without involving any tedious methods.

SUMMARY OF THE INVENTION

In accordance with the above and other objects, the present invention provides a novel process for isolation of 10-deacetyl baccatin-III (10-DAB) and also complete separation of paclitaxel present in the primary extract, on a commercial scale from plant extract of Taxus species by solvent crystallization without employing chromatographic separation.

DETAILED DESCRIPTION OF THE INVENTION

The present invention provides a novel process for the isolation of 10-deacetyl-baccatin III, a compound used for the synthesis of paclitaxel and docctaxel analogues.

A novel process for isolation of 10-deacetyl baccatin-III (10-DAB) and also complete separation of paclitaxel present in the primary extract, on a commercial scale from plant extract of Taxus species, said process comprising the steps of preparing an alcoholic extract of the dried leaves of *Taxus baccata*, treatment thereof with aliphatic ketones, evaporation of the mother liquor to yield an residue which is treated with aqueous ketonic solvent mixture, separation of insolubles, extracting aqueous ketonic solvent with organic solvent followed by selective crystallization for isolation of 10-DAB. The process is simple and 10-deacetyl baccatin-III can be selectively isolated from the recoverable part of a plant of Taxus species by crystallization. The present process involves the steps of (a) extracting the pulverised and optionally dried parts of a plant of Taxus species, with aliphatic alcohol (b) preparing a partially concentrated alcoholic extract containing 10-DAB, (c) treating extract with aliphatic ketones and separating the insolubles from the mother liquor by centrifugation or filtration, (d) treating the residue obtained after evaporation of the mother liquor of step (c) with a mixture of aliphatic ketones and water, and removing the insolubles through a celite bed by filtration or centrifugation, which is enriched in paclitaxel content.

(e) extraction of the aqueous ketonic solution which is totally devoid of paclitaxel, with aromatic hydrocarbons to remove color substances, followed by the extraction of aliphatic ester or chlorinated solvents.

(f) evaporating the organic layer of (e) to dryness to obtain a semisolid residue from with 10-DAB is obtained by selective crystallizations, and (g) isolation and purification of 10-DAB The insoluble obtained in step (d) after treating with mixture of aliphatic ketones and water has the advantage of exclusively separating paclitaxel from 10-deacetyl baccatin-III present in the primary alcoholic extract. The insoluble is separately subjected to purification leading to the isolation of pure paclitaxel. Thus above process leads to isolation paclitaxel and 10-DAB from the natural source.

In addition, use of acetone in step (C) in the present process has a specific advantage of separating 10-DAB and paclitaxel from the primary alcoholic extract with a lesser percentage of accompanying impurities.

In one embodiment, the aliphatic alcohol used for preparation of a alcoholic extract is selected from the group consisting of methanol, ethanol, propanol, isopropanol and tertiary butanol.

In one feature, the aliphatic alcohol is methanol.

In another embodiment, the alcoholic extract is obtained by stirring the pulverised and optionally dried parts of the plant of the Taxus species in methanol, ethanol, propanol, isopropanol or butanol.

In another feature of the invention, the crystallization of 10-DAB is carried out by treatment of the residue with aliphatic nitrile solvents optionally mixed with aliphatic alcohols selected from the group consisting of methanol, isopropanol, butanol, or aliphatic esters selected ethyl acetate, propionyl acetate and isoamyl acetate. The aliphatic nitriles may be selected from acetonitrile and propionitrile.

In yet another feature, DAB is extracted from any part of any plant of the genus Taxus.

In another feature, 10-DAB is isolated by crystallization followed by centrifugation. In another feature, the parts of the plant are the leaves.

In another feature, the paclitaxel is completely separated from 10-DAB which is coexisting in the primary extract.

The process illustrated above for isolation of 10-deacetyl baccatin-III (10-DAB) does not involve any chromatographic technique at any stage.

The preferred process comprises of following steps.

1. The leaves of *Taxus baccata* are pulverised and may be optionally dried. Water miscible aliphatic alcohol selected from methanol, ethanol, propanol, isopropanol, butanol, is added to ground leaves and the mixture is stirred for 12 hours. The preferred aliphatic alcohol used in the present process is methanol.

2. The semi-concentrated alcoholic extract so obtained contains 10-DAB, paclitaxel, and other taxanes. The said extract is stirred with aliphatic ketone for one hour. The insoluble material is then separated out by filtration through a celite bed or centrifugation. The liquid left behind is the mother liquor which is then used for further processing.

3. Mother liquor of step (2) is evaporated under vacuum to yield a residue which is treated with a mixture of aqueous ketonic solvents and the insolubles are removed by filtration or centrifugation through a celite bed containing enriched paclitaxel which is further processed to yield paclitaxel. The clear aqueous ketonic solution obtained here may be used for further processing to isolate 10-DAB.

4. Clear aqueous ketonic solution which is completely devoid of paclitaxel obtained is extracted with aromatic hydrocarbon to remove less polar substances other than 10-DAB. Then the remaining aqueous ketonic phase is treated with water immiscible solvent, preferably, aliphatic ester or chlorinated solvent, to extract 10-DAB completely.

5. Thereafter, the organic solvent extract is evaporated under vacuum to dryness at 80°–90° C. to yield a semisolid residue. Subsequently, crude 10-DAB is selectively crystallised from the residue obtained above by treating it with aliphatic nitrile solvent such as acetonitrile, propionitrile optionally mixed with an aliphatic alcohol such as methanol, isopropanol, n-butanol or aliphatic ester such as acetone, ethyl acetate, butyl acetate. It is advantageous to perform the selective crystallization in acetonitrile, optionally in the presence of ethanol, methanol or ethyl acetate, and/or butyl acetate. The 10-DAB is purified by any conventional method such as crystallization followed by centrifugation.

The above novel process for the isolation of 10-DAB can be applied for extraction from any part of the plant Taxus sp. esp *T. baccata, T. brevifolia, T. cannadensis, T. cuspidata, T. floridara, T. media* or *T. wallichiana*. The process described above, is simple and does not involve any chromatography at any stage and can be obtained using only solvents.

The other advantage of the present process is that the solvents used in various steps can be reused. In addition, the applicant has identified that though the raw material used in the present invention contains 10-DAB and paclitaxel and the isolation of the latter commercially could also be achieved successfully, whereas such achievements, is not envisaged on the prior art to the invention.

The above novel process is described in detail by the following examples which are provided for illustration only and should not be construed to limit the scope of the present invention.

EXAMPLE I

The Leaves of *Taxus baccata* are pulverised and optionally dried. Preferably, the mean particle size of the leaves is close to 0.6 mm to 0.8 mm. An alcoholic extract is prepared by stirring 1000 L of methanol with 100 kg. of the ground the leaves (rotation of 58 per minute) at ambient temperature (15 to 45° C.) in the reactor for 12 hrs. The methanolic solution collected after centrifugation is evaporated under reduced pressure (150 m bar) at 40–50° C. in an evaporating reactor to obtain a semi concentrated extract whose weight is between 20–30% of the weight of leaves.

The 25 kg. of semiconcentrated methanolic extract containing 0.12% of 10-deacetyl baccatin-III, 20% of water and 10% of methanol (prepared under the conditions described above) is stirred (58 rpm) with 175 L. (liter) of acetone at ambient temperature for 1 to 2 hrs. The insoluble solid that appears is separated by filtration or centrifugation. The acetone soluble in mother liquor forming 35% of the weight of the semi concentrated extracted is distilled off to dryness at 40–50° C. under vacuum (150 m bar).

8.75 kg of dry residue obtained is stirred with the 43.75 L. of acetone and demineralized water (DM) mixture (ratio preferably 2:8) for 2 hr. at ambient temperature at high rpm (72 revolution per minute). The insoluble material is removed by filtration or centrifugation on celite bed. The insolubles containing enriched paclitaxel is processed further to isolate commercial levels of paclitaxel. The aqueous ketonic mother liquor collected is clear dark red.

The aqueous ketonic layer which is completely devoid of paclitaxel is extracted twice with 17.5 L. and once with 8.75 L. (liter) of toluene by stirring (40 revolution per minute) for 1 hour each extraction.

The aqueous ketonic layer obtained after toluene extraction, is then extracted with methylene chloride (4×16.5 L) at ambient temperature (15 to 45° C.) for 30 minute each extraction by stirring at (40 revolution per minute). The methylene chloride, layer is combined and dried over sodium sulphate and then evaporated to dryness under vacuum (150 m bar) at 25° C. to 65° C. in a evaporating flask. The weight of the methylene chloride residue usually lies between 1.5 to 1.8 w/w % of the semi concentrated methanol extract, containing 4.5 to 6% of 10-deacetyl baccatin-III.

EXAMPLE II 468.7 g of dry extract containing 5.1% of 10-deacetyl baccatin-III is obtained under the conditions described in example I. The extract is stirred 40 revolution for minute with 975 ml of acetonitrile at 50–60° C. When the extract is completely dissolved, the mixture is cooled at 0–5° C. for 12–16 hrs. and stirred at very low rpm (20). The solid insoluble are separated out by filtration or centrifugation and washed with 50 ml of acetonitrile. A crude solid (29.43 g) is obtained after drying it at reduced pressure (0.5 m bar) at 60–70° C. for 12 hrs. having 76.1% of 10-deacetyl baccatin-III.

EXAMPLE III 29.43 g of crude solid obtained under the condition described in example II, are dissolved in 735.5 ml of methanol by refluxing at 70° C. for 1 hr with stirring (rpm-58). The solution is cooled to ambient temperature (15 to 45° C.) and then filtered through celite bed to obtain clear solution. The filtrate is stirred at very low rpm (20) and 295 ml of acetonitrile is slowly added to it. The mixture is then cooled to 0–5° C. and maintained for 12–15 hrs. The precipitate is separated by filtration or centrifugation and washed with 10 ml mixture of methanol acetonitrole (1:1). The product is dried at reduced pressure (0.5 m bar) at 90–95° C. for 20–30 hr. 22.2 g of off white final product is thus obtained, containing 94.1% of 10-deacetyl baccatin-III.

The mother liquor obtained after final crystallization is evaporated to dryness, and recycled for purification of 10-deacetyl baccatin-III.

EXAMPLE IV 30 g of crude solid obtained under the condition described in Example II, is dissolved in 750 ml of acetone by refluxing at 65° C. for 1 to 2 hr. The solution is cooled to room temperature and then filtered through a celite bed. Filtrate is stirred at very low rpm (20) and acetonitrile (200 ml) is slowly added to it. Temperature of the solution is brought down to 0–5° C. and maintained up to 15–20 hrs. The precipitate is separated out by centrifuging and wash the sold with 1:1 mixture of acetone and acetonitrile. The final product is dried under vacuum (0.5 m bar) at temperature 80–90° C. for 12–20 hrs. The final (23.1 g) product is thus obtained, containing 93.5% of 10-deacetyl baccatin-III.

ADVANTAGES OF THE NOVEL PROCESS a) It is simple, cost effective and has commercial feasibility.

b) It does not involve tedious process of chromatographic technique at any stage of this process.

c) In this process, there is reusability of the solvent in many steps.

d) This process is applicable for extraction of any part of the plant of different species of Taxus.

e) This process can be used to separate natural paclitaxel present in the primary alcoholic extract.

f) Depending on the quality of raw material yield of 10-deacetyl baccatin-III varies from 60% to 90% of the content of raw material.

What is claimed is:

1. A process for the isolation of 10-deacetyl baccatin-III from the recoverable part of a plant of Taxus species by crystallization comprising the steps of:
    (a) extracting the pulverised and optionally dried parts of a plant of Taxus species, with aliphatic alcohol,
    (b) preparing a partially concentrated alcoholic extract containing 10-DAB and paclitaxel,
    (c) treating extract with aliphatic ketones and separating the insolubles from the mother liquor by centrifugation or filtration,
    (d) treating the residue obtained after evaporation of the mother liquor of step (c) under vacuum with a mixture of water and aliphatic ketones solvent and removing the insolubles through a celite bed by filtration or centrifugation, the insolubles containing enriched paclitaxel residue which is further processed to obtain commercial quantities of paclitaxel,
    (e) extraction of the aqueous ketonic solution devoid of paclitaxel with aromatic hydrocarbons to less polar substances, followed by extraction with water immiscible aliphatic esters or chlorinated solvents,
    (f) evaporating the organic layer of (e) to dryness to obtain a semisolid residue from which crude 10-DAB is obtained by selective crystallizations, and
    (g) isolation and purification of 10-DAB.

2. A process as claimed in claim 1, wherein the aliphatic alcohol used for preparation of a alcoholic extract is selected from the group consisting of methanol, ethanol, propanol, isopropanol and butanol.

3. A process as claimed in claim 1, wherein the aliphatic alcohol used is methanol.

4. A process as claimed in claim 1, wherein the alcohol extract is obtained by stirring the pulverised and optionally dried parts of the plant of the Taxus species in methanol, ethanol, propanol, isopropanol or butanol.

5. A process as claimed in claim 1, wherein the selective crystallization of 10-DAB is carried out by treating of the semisolid residue with aliphatic nitrile solvent optionally mixed with aliphatic alcohols.

6. A process as claimed in claim 1, wherein the aliphatic nitrile solvent is selected from acetonitrile or propionitrile.

7. A process as claimed in claim 1, wherein nitrile solvent is mixed with aliphatic alcohols selected from the group consisting of methanol, isopropanol, butanol or with aliphatic esters selected from ethyl acetate, propionyl acetate and isoamyl acetate.

8. A process as claimed in claim 1, wherein 10-DAB is extracted from any part of any plant of the genus Taxus.

9. A process as claimed in claim 1, wherein 10-DAB is isolated by crystallization followed by centrifugation/filtration.

10. A process as claimed in claim 1, wherein the plant is *Taxus baccata*.

11. A process as claimed in claim 1, wherein the parts of the plant are the leaves.

\* \* \* \* \*